(12) United States Patent
Hwang et al.

(10) Patent No.: US 6,462,238 B2
(45) Date of Patent: Oct. 8, 2002

(54) PROCESS FOR THE REDUCTION OF CYANO-SUBSTITUTED SULFONES TO AMINOALKYLENE-SUBSTITUTED SULFONES

(75) Inventors: Jack (ChanKou) Hwang, Boulder; Eugene Tarlton, Louisville; Anthony D. Piscopio, Longmont, all of CO (US)

(73) Assignee: Array BioPharma, Inc., Boulder, CO (US)

( * ) Notice: Subject to any disclaimer, the term of this patent is extended or adjusted under 35 U.S.C. 154(b) by 0 days.

(21) Appl. No.: 09/843,986

(22) Filed: Apr. 27, 2001

(65) Prior Publication Data

US 2002/0013498 A1 Jan. 31, 2002

Related U.S. Application Data

(60) Provisional application No. 60/201,137, filed on May 2, 2000.
(51) Int. Cl.⁷ .............................................. C07C 209/48
(52) U.S. Cl. ....................................... 564/416; 564/493
(58) Field of Search .................................. 564/493, 416

(56) References Cited

U.S. PATENT DOCUMENTS 4,372,893 A * 2/1983 Eckert ........................ 558/302

FOREIGN PATENT DOCUMENTS

| EP | 0 639 562 A1 | * 2/1995 | ......... C07C/317/44 |
| WO | 9935146 | 7/1999 | |

OTHER PUBLICATIONS

H.C. Brown, et al., *Synthesis*, No. 8, 605–606, Aug. 1981.
Gardner, et al., *Can. J. Chem.* 51:1419, 1973.
Bordwell, et al., *J. Am. Chem. Soc.*, 73:2251, 1951.
A. Dhainaut, et al., *J. Med. Chem.*, 35 (13):2481–2496, 1992.
Database CAPLUS on STN, Acc. No. 1995:494622, Kunde, 'Oxidative preparation of 2–cyanoethyl–2'–hydroxyethylsulfone and its hydrogenation to 3–aminopropyl–2'–hydroxyethylsulfone.' EP 639562 A1 (abstract).*
Database CASREACT on STN, 222:239194, EP 639562 A1, reaction 2 of 6.*

* cited by examiner

*Primary Examiner*—Brian J. Davis
(74) *Attorney, Agent, or Firm*—McDonnell Boehnen Hulbert & Berghoff

(57) ABSTRACT

Disclosed is a process for selectively reducing a nitrile containing organic compound that also contains a sulfone moiety, the nitrile being reduced to a primary amine.

16 Claims, No Drawings

PROCESS FOR THE REDUCTION OF CYANO-SUBSTITUTED SULFONES TO AMINOALKYLENE-SUBSTITUTED SULFONES

BACKGROUND OF THE INVENTION

1. Field of the Invention

This invention relates generally to a process for the reduction of nitriles to amines. This invention further relates to a process for the reduction of a nitrile without reducing a sulfone also present in the molecule.

2. Summary of the Related Art

The reduction of nitrites is an extremely important synthetic tool for the production of primary and secondary amines, as well as alcohols. In particular, the hydrogenation of a nitrile group to the corresponding primary amine is very well known in the art. For example, hydride compounds such as lithium aluminum hydride or aluminum hydride have been employed. Another conventional method for the reduction of a nitrile is use of an alkali metal such as lithium, sodium or calcium in aqueous ammonia or an amine solvent. Yet another reducing agent for nitriles, and perhaps the most well known and documented procedure, is catalytic hydrogenation.

The use of borane ($BH_3$) and substituted boranes have been used to reduce aldehydes and ketones to the corresponding alcohols. Similarly, oximes can also be reduced by borane to yield the respective hydroxylamine. Substituted boranes have also been used to reduce nitriles to primary amines (Brown et al., *Synthesis* 1981, 605). Reagents such as sodium borohydride, however, do not generally reduce nitrites unless the reaction is carried out in an alcoholic solvent when a $CoCl_2$ catalyst is added or in the presence of Raney nickel.

As with any organic synthetic reaction, the key of the reduction is to selectively reduce the desired functional group without reducing or in any way altering other functional groups in the molecule. An example of another functional group that is susceptible to reducing agents is the sulfone group.

Common reagents that can reduce a sulfone to its respective sulfide are diisobutyl aluminum hydride (Gardner et al., *Can. J. Chem.* 1973, 51, 1419) and lithium aluminum hydride (Bordwell et al., *J. Am. Chem. Soc.* 1951, 73, 2251). Heating with elemental sulfur can also reduce sulfones. Sulfones with a β-hydrogen can also undergo elimination reactions and are thus susceptible to cleavage, particularly at higher temperatures.

Due to the large technical and industrial importance of amines, new and improved methods for their production are desired. However, it is often necessary to reduce a nitrile in a molecule without affecting another reducible group. The technology of hydrogenating nitriles has been a convenient route to affording primary amines, but high temperatures involved in catalytic hydrogenation and the ability of alkali metals and many hydride compounds to affect different functionalties increases the need for a more selective nitrile reducing process For example, the preparation of sulfonethylamines is a necessary intermediate for the preparation of certain tyrosine kinase inibitors (Carter, M. et al., WO 99/35146). However, applying standard nitrile reduction techniques to α-sulfonitriles produces an unwanted isomerization of the metalloimine intermediate to the corresponding vinylogous amide. Thus, to date, an alternate multi-step approach is necessary for synthesizing these compounds.

Finally, the use of nucleophillic reducing agents such as sodium borohydride or lithium aluminum hydride requires the removal of salts by washing with water; many amine products (particularly aminoalkylene substituted sulfones) are soluble in water and therefore a non-aqueous work-up is desired.

SUMMARY OF THE INVENTION

It is an object of the present invention to provide a process for the selective reduction of nitrites to amines. According to the present invention, there is provided a process for the reduction of a nitrile containing organic compound without reducing a sulfone also present in the molecule.

It is a further object of the present invention to provide a process of reducing a 2-(substitutedsulfonyl)ethanenitrile to the corresponding amine without isomerizing a metalloimine intermediate to a vinylogous amide.

It is still further an object of the present invention to provide a process for the selective reduction of nitrites to amines that employs a non-aqueous workup.

It is still another object of the invention to provide a convenient, efficient and economical one-step process to prepare sulfonoethylamines as intermediates for various biologically active compounds (see Carter, M. et al., WO 99/35146).

The invention process generally involves subjecting a cyanoalkylsulfone to borane-tetrahydrofuran complex, neat or in a suitable inert solvent, and then purifying the resulting crude product to afford the desired aminomethylenealkylsulfone.

In a preferred embodiment of the invention, a 2-(substitutedsulfonyl)ethanenitrile is reduced to aminoethyl methylsulfone with borane-tetrahydrofuran complex.

DETAILED DESCRIPTION OF THE INVENTION

The novel feature of the present process resides in the employment of borane or substituted borane for the hydrogenation of a nitrile containing organic compound that also contains a sulfone moiety. The object of the process is to keep the sulfone intact while selectively reducing the nitrile group to the respective primary amine.

Accordingly, one embodiment of the present invention is a process for the preparation of a compound of the formula I

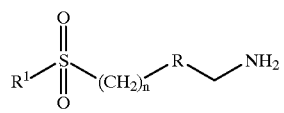

which comprises reacting a compound of the formula II

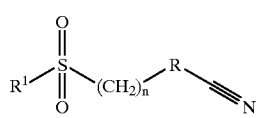

with about 1 to 2 equivalents borane or a substituted borane neat or in a substantially inert organic solvent at a temperature of about −10° C. to 60° C. wherein R and $R^1$ are independently lower alkyl, cycloalkyl, aryl, heteroaryl, arylalkyl, or heteroarylalkyl; and n is 0–6.

The term "borane" or "diborane" in the present invention refers to the chemical reagent with the formula $BH_3$. By "substituted borane" is meant a compound that includes but is not limited to the following: borane-methyl sulfide complex, borane-dimethylsulfide complex, borane-morpholine complex, borane-piperdine complex, borane-pyridine complex, borane-tetrahydrofuran complex, borane-triethylamine-complex and borane-trimethylamine complex. A preferred substituted borane for the present invention is borane-tetrahydrofuran complex. Borane can be purchased (e.g. Aldrich Chemical Company) or prepared in situ by reacting sodium borohydride and boron trifluoride diethy letherate.

By "alkyl", "lower alkyl", and "$C_1$–$C_6$ alkyl" in the present invention is meant a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, iso-pentyl, n-hexyl, and the like. The alkyl group can be optionally mono-, di-, or trisubstituted with, e.g., halogen, lower alkyl, lower alkoxy, lower alkylthio, trifluoromethyl, amino, mono- or dialkylamino and hydroxy.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or N, examples being oxiranyl, pyrrolidinyl, piperidyl, tetrahydropyran, and morpholine.

By heteroaryl is meant one or more aromatic ring systems of 5-, 6-, or 7- membered rings containing at least one and up to four heteroatoms selected from nitrogen, oxygen, or sulfur. Such heteroaryl groups include, for example, thienyl, furanyl, thiazolyl, imidazolyl, (is)oxazolyl, tetrazolyl, pyridyl, pyrimidinyl, (iso)quinolinyl, napthyridinyl, phthalimidyl, benzimidazolyl, benzoxazolyl. The heteroaryl can be mono-, di-, or trisubstituted with, e.g., halogen, lower alkyl, lower alkoxy, lower alkylthio, trifluoromethyl, aryl, heteroaryl, amino, mono- or dialkylamino and hydroxy.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can be mono-, di-, or trisubstituted with, e.g., halogen, lower alkyl, lower alkoxy, lower alkylthio, trifluoromethyl, aryl, heteroaryl, amino, mono- or dialkylamino and hydroxy. A preferred aryl is phenyl.

By "inert organic solvent" is meant an organic solvent which, under the reaction conditions of the process, does not enter into any appreciable reaction with either the reactants or the products. A substantially anhydrous aprotic organic solvent is preferred. The term "substantially anhydrous" as used in the present description means that, although anhydrous organic solvents are generally preferred, trace amounts of water, such as that often found in commercially available solvents, can be tolerated. Although the borane and substituted borane reagents described herein will react with any water present in the solvent medium, additional amounts of the reagent can easily be added to compensate for the loss due to hydrolysis.

Suitable solvents include, but are not limited to, aliphatic and aromatic solvents such as pentane, hexane, heptane, cyclohexane, benzene, toluene, xylenes, mesitylene and the like; cyclic and acyclic ethers such as diethyl ether, butyl ethyl ether, tetrahydrofuran, dioxane and the like; and halogenated hydrocarbons such as chloroform, methylene chloride, carbon tetrachloride and the like. A preferred class of solvents is the ethers. A most preferred solvent is tetrahydrofuran.

In a preferred embodiment, the present invention provides a process for preparing a compound of the formula

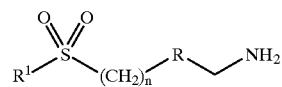

I which comprises reacting a compound of the formula

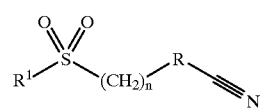

II with about 1 to 2 equivalents borane or a substituted borane neat or in a substantially inert organic solvent at a temperature of about −10° C. to 60° C. to afford an amino-boron intermediate;

hydrolyzing the amino-boron intermediate with an acid to form a salt of the amine; and neutralzing the salt of the amine with a suitable base to form a compound of formula I wherein R, $R^1$ and n are as defined above.

In a more preferred embodiment of the invention, n is 0 or 1 and R is lower alkyl. In an even more preferred embodiment, n is 0 and R is methylene.

In another more preferred embodiment of the invention, the borane reduction is carried out at a temperature of about 0° C. to 55° C. Most preferably, the reaction is initially carried out at a temperature of between 45° C. to 50° C. and then allowed to cool to ambient temperature. The initial elevated temperature of 45° C. to 50° C. is maintained by the slow addition of the borane or substituted borane.

In yet another more preferred embodiment of the invention, the hydrolization of the amino-borane intermediate is achieved with an anhydrous alcoholic acid, such as, for example, hydrogen chloride in methanol, hydrogen chloride in ethanol, hydrogen chloride in isopropanol and aqueous hydrogen chloride.

In yet another particular embodiment of the present process, the base used to neutralize the salt of the amine is preferably dissolved in an aqueous phase either by charging to the reaction vessel along with the other components including water or by predissolving it in water to be added as an aqueous solution. Typical classes of such bases include, but are not limited to, the alkali metal hydroxides, the alkali metal alkoxides, the alkaline earth metal hydroxides, the alkali metal carbonates and bicarbonates and the quaternary ammonium hydroxides. Illustrative but not limiting thereof are sodium hydroxide, sodium carbonate, sodium bicarbonate, potassium hydroxide, lithium hydroxide, sodium methoxide, sodium ethoxide, sodium butoxide, potassium methoxide, potassium ethoxide, calcium and barium hydroxides, tetrabutyl ammonium hydroxide and the like. Most preferred bases of the present process are sodium methoxide and sodium carbonate.

The neutralization of the salt typically is carried out in a protic organic solvent miscible with water, such as, for example, methanol. The pH of aqueous/aprotic organic solvent mixture is brought to about 8.0 to 10.0 with the suitable base, preferably about 9.0.

The examples presented below are intended to illustrate particular embodiments of the invention, and are not intended to limit the scope of the specification or the claims in any way.

An illustration of the process of the present invention is shown in Scheme I. R, $R^1$ and n are as defined above.

Scheme 1

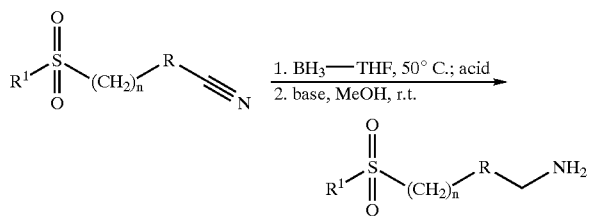

Those having skill in the art will recognize that the starting materials and reagents may be varied, as demonstrated by the following examples.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples for the process of the invention are set forth below.

EXAMPLES

Example 1

To a dry 20 liter reactor is added a 1.0 M solution of $BH_3 \cdot THF$ in THF (12.6 mol, 12.6 liters, 2 equivalents). The solution is heated to 40° C. before the addition of 2-(methylsulfonyl)ethanenitrile (6.3 mol, 750 g, 1 equivalent). The addition of the nitrile is added at such a rate to maintain an internal reaction temperature of about 45–50° C. The reaction is then allowed to cool to room temperature and is stirred for an additional 12 hours. Thin layer chromatography (7:2:1 dichloromethane/methanol/triethylamine as eluent) reveals consumption of starting material. The reaction mixture is then slowly added to a 20 liter round bottom flask containing methanol (4 liters). The solvent is then removed in vacuo until about 1 liter of volume is left. Methanol (4 liters) is then added and subsequently removed. This addition and removal of methanol is repeated another three times before the amino-boron intermediate is taken up in methanol (2 liters). The mixture is then treated with a solution of anhydrous HCl (890 g) in methanol (3 liters) and refluxed for one hour. The solution is cooled, concentrated and re-subjected to anhydrous HCl (890 g) in methanol (3 L) and refluxed for one hour. Subsequent cooling of the reaction mixture is followed by dilution with dichloromethane (4 liters). Precipitated solids are filtered and washed with 500 mls of 1:1 dichloromethane/methanol to afford 855.2 g of the hydrochloride salt of the desired amine. The salt is then dissolved in methanol (3 liters) and neutralized with a 4 M solution of sodium methoxide in methanol until the pH reaches about 9.0. Dichloromethane (3 liters) is then added to the mixture and the precipitated inorganic salts are then filtered (GF/F filter paper). The filtrate is concentrated in vacuo and the residue is redissolved in 4:1 dichloromethane/methanol (2 liters). The precipitated inorganic salts are filtered and the filtrate is concentrated to yield 603.6 g of 1-(methylsulfonyl)eth-2-ylamine (77.89%). GC-Flo=98% pure. 1H NMR (DMSO) δ 2.27 (s, 2, broad), 2.93 (t, 2), 2.97 (s, 3), 3.14 (t, 2).

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A process for the preparation of a compound of the formula

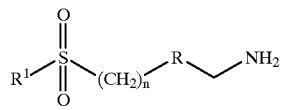

which comprises reacting a compound of the formula

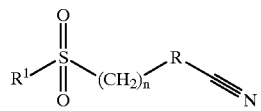

with about 1 to 2 equivalents of a reducing reagent selected from borane and a substituted borane at a temperature of about −10° C. to 60° C., wherein R and $R^1$ are independently lower alkyl, cycloalkyl, aryl, heteroaryl, arylalkyl, or heteroarylalkyl; and n is 0–6.

2. A process according to claim 1 in which the reducing agent is a substituted borane.

3. A process according to claim 2 in which the reducing agent is borane-tetrahydrofuran complex.

4. A process according to claim 1 in which the temperature is from about 45° C. to 50° C.

5. A process according to claim 1 in which about 2 equivalents of reducing agent is used.

6. A process according to claim 1 in which n is 0 or 1 and R is lower alkyl.

7. A process according to claim 6 in which n is 0 and R is methylene.

8. A process for the preparation of an amine compound of the formula

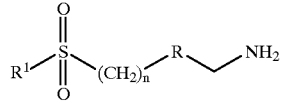

which comprises reacting a compound of the formula

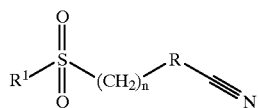

with about 1 to 2 equivalents borane or a substituted borane neat or in a substantially inert organic solvent at a temperature of about −10° C. to 60° C. to afford an amino-boron intermediate;
hydrolyzing the amino-boron intermediate with an acid to form a salt of the amine; and
neutralzing the salt of the amine with a suitable base to form the nitrile compound wherein R and $R^1$ are independently lower alkyl, cycloalkyl, aryl, heteroaryl, arylalkyl, or heteroarylalkyl; and
n is 0–6.

9. A process according to claim 8 in which the reducing agent is a substituted borane.

10. A process according to claim 9 in which the reducing agent is borane-tetrahydrofuran complex.

11. A process according to claim 8 in which the temperature is from about 45° C. to 50° C.

12. A process according to claim 8 in which about 2 equivalents of reducing agent is used.

13. A process according to claim 8 in which n is 0 or 1 and R is lower alkyl.

14. A process according to claim 13 in which n is 0 and R is methylene.

15. A process according to claim 8 in which the acid is anhydrous HCl.

16. A process according to claim 8 in which the base is selected from the group consisting of sodium methoxide or sodium carbonate.

* * * * *